United States Patent [19]

Allen

[11] Patent Number: 5,409,664

[45] Date of Patent: Apr. 25, 1995

[54] LAMINATED ASSAY DEVICE

[75] Inventor: Michael P. Allen, Sunnyvale, Calif.

[73] Assignee: Chemtrak, Inc., Sunnyvale, Calif.

[21] Appl. No.: 128,373

[22] Filed: Sep. 28, 1993

[51] Int. Cl.[6] ...................... G01N 21/75; G01N 33/92
[52] U.S. Cl. ........................................ 422/56; 422/58;
    436/71; 436/170; 436/178; 436/805; 436/810;
    435/11; 435/19; 435/28; 435/805; 435/970
[58] Field of Search .................... 422/55, 56, 58, 61;
    436/63, 71, 74, 169, 170, 178, 805, 810; 435/4,
    11, 805, 970, 19, 28

[56] References Cited

U.S. PATENT DOCUMENTS

| | | | |
|---|---|---|---|
| 4,973,549 | 11/1990 | Khanna et al. | 435/11 |
| 4,987,085 | 1/1991 | Allen et al. | 436/169 |
| 4,999,287 | 3/1991 | Allen et al. | 435/11 |
| 5,132,086 | 1/1992 | Allen et al. | 422/56 |
| 5,215,886 | 6/1993 | Patel et al. | 435/11 |
| 5,234,813 | 8/1993 | McGeehan et al. | 435/7.9 |

Primary Examiner—David A. Redding
Attorney, Agent, or Firm—Bertram I. Rowland

[57] ABSTRACT

A laminated assay device for use in determining the presence or amount of an analyte in a sample involving a bibulous assay strip having a sample application zone, a reagent zone and a pair of liquid impervious barriers defining a measurement zone extending from and in fluid communication with the application zone. The measurement zone has a volume measuring the amount of sample required for the assay. A substantially nonabsorbent first supporting film extends across and is laminated to the front surface of the assay strip, while a substantially nonabsorbent second supporting film extends across and is laminated to the back surface of the assay strip. The assay strip is impregnated with the members of a signal producing system which, upon reaction with a component in the sample, produce a detectable signal.

20 Claims, 4 Drawing Sheets

LAMINATED ASSAY DEVICE

TECHNICAL FIELD

The field of the subject invention concerns diagnostic assay strips permitting visual measurement of the amount of an analyte in a biological fluid.

BACKGROUND

Efficiently and accurately determining the presence or amount of an analyte in a biological sample has become increasingly important. Often, an assay must be performed in a clinical laboratory to obtain an accurate quantitative measurement. When the protocol requires the addition of measured amounts of sample and reagents, a skilled technician must usually perform the assay to guarantee a reliable result. The measurement of an analyte in a biological fluid plays an increasingly important role in the treatment and therapy of numerous medical conditions. The ability to quickly make a qualitative or quantitative determination, in the home or doctor's office, of the presence or amount of an analyte in a sample is of great interest.

An assay which may be accurately and efficiently performed outside of the clinical laboratory would provide results which may be immediately addressed by the physician and patient. To guarantee the accuracy of the assay determination, the system should have an integral control or standard by which the assay determination may be verified. The control would assure that the device was operated as intended, that there has been no spoilage or contamination of the device such as through improper storage and handling, and that the results may be relied upon. A system which may be used in a doctor's office or in the home should have a simple protocol which does not require the measurement of either sample or reagents. Systems have been developed for performing numerous assays outside of the clinical laboratory. Nevertheless, there is continuing interest in providing improved and alternative methods to those which are presently generally available.

In addition, the devices will be for single use and be disposed of after the use. For this purpose, the device must be capable of being efficiently manufactured in an economic manner and be relatively small, so as to minimize the disposal volume. The manufacturing process should be simple to minimize failures and enhance reproducibility of the devices, so that there is a low failure rate during production.

The determination of cholesterol levels in blood provides one example where there is an interest in an accurate and reliable system which provides immediate results. There has been an increasing awareness that the level of total blood cholesterol, primarily the LDL fraction, should be maintained within a specific range to promote the health of the individual and reduce the risks of coronary artery disease. Recognition of individuals with high blood cholesterol levels is important, since the cholesterol level may be controlled by adjusting the diet and/or administering cholesterol lowering drugs. A system which may be easily and conveniently used by an individual at home to monitor his cholesterol level would provide a significant tool in aiding the individual to maintain a healthy blood cholesterol level. The use of such a system in the doctor's office would also be particularly useful for efficiently identifying and monitoring the treatment of individuals with high blood cholesterol.

The monitoring of blood cholesterol levels provides one example of where there is a need for a reliable system which may be used outside of the clinical laboratory. The determination of the presence or amount of numerous other analytes in a biological sample is also of great interest.

Relevant Literature

U.S. Pat. Nos. 4,987,085, 4,973,549, 4,999,287, 5,132,086, 5,215,886, 5,234,813 and the references cited therein.

SUMMARY OF THE INVENTION

The present invention involves methods and apparatus for use in detecting the amount of an analyte in a biological sample by using a laminated bibulous assay strip impregnated with the members of a signal producing system. The device will have primarily three layers, upper and lower plastic support layers having appropriate openings for sample application, viewing and an air vent and an intermediate bibulous layer with at least one narrow channel defined by liquid impervious borders in the bibulous layer. Usually there will be small additional staggered layers for recieving and processing the sample. The absorption volume of the laminated assay strip determines the amount of sample required for the assay. The assay strip has a continuous sample path which provides a measurement of the analyte in the sample, and desirably a continuous control flow path providing for simultaneous verification of the operability of the device. The sample is applied at one end of the assay strip and moves through the strip by wicking action. The reaction of a component in the sample with members of the signal producing system produces a detectable signal downstream of the sample application site. Improved accuracy and efficiency are obtained by having a simultaneous control, impregnating the assay strip with the reagents needed to produce the detectable signal and by having as the only assay step the application of a minimal amount of sample.

BRIEF DESCRIPTION OF THE DRAWINGS

FIG. 4c is an exploded elevational end view of the assay device of FIG. 4a;

DESCRIPTION OF SPECIFIC EMBODIMENTS

Methods and apparatus are provided for the determination of the amount of an analyte in a sample employing a bibulous assay strip with a continuous sample flow path having a sample application zone, a reagent zone and a measurement zone. The device has three primary layers, a lower plastic support, a main bibulous layer having a defined channel for the measurement region, and an upper plastic support having appropriate openings for sample application, air escape and, as appropriate viewing of the measurement region or other appropriate sites.

As defined herein, the assay strip is the flowpath of the sample and will usually comprise at least two separate components with a blood sample, but may comprise four or more separate components, each in the same or a different plane, for receiving the sample, filtering cells from a sample, where blood is the sample, and where the analyte is a reactant to produce a detectable signal, a reagent strip which will process the analyte. Front and back supports are laminated to the assay strip. The absorption volume of the reagent and measurement zones determines the amount of sample processed in the assay. At the appropriate sites, the assay strip is impregnated with the necessary reagents for producing a color front or discernable border of a detectable signal system downstream of the sample application site. The presence of an analyte in the sample, for example cholesterol, results in the production of a color front in the measurement zone. The distance of the boundary from a predetermined site is related to the amount of analyte within the sample.

A continuous control path may also be included to verify the operability of the device and the accuracy of the measurement in the sample path. Verification is provided by the appearance of a color front at a predetermined location along the measurement region of the control path. Preferably, a simple and reliable protocol related to the sample path assay protocol is used to achieve the control. Since the control and sample paths will be affected by the same factors, such as test conditions, storage history and the like, substantially analogous path protocols should be incorporated for the control and sample paths. In order to provide a known standard, the control path will be different in some aspects from the sample path. For example, the sample flow path receives a sample having an unknown quantity of analyte, while a known amount of a compound is provided in the control path. The compound found in the control path may be the same compound as the analyte, or a different compound that can be related to a known amount of the analyte. See, for example, co-pending application Ser. No. 08/015,696, filed Feb. 9, 1993.

The amount of various analytes in a biological sample may be determined using the assay device. In addition, various chemistries may be employed, using different types of reagent systems to produce the desired signal. The non-instrumented assay may be quantitative or semi-quantitative.

The flow path of the assay device generally has three regions: a sample application zone, a reagent zone and a measurement zone. The flow path may comprise one or more reagent zones, where a reagent zone may partially include the sample application zone. The device is configured for ease of manufacturing. The various stages in producing and assembling the parts minimize the possibility of failure due to premature reagent interactions. For the most part, two different configurations are preferred. In the first configuration, the assay strip is in a single plane, where each of the regions is part of a bibulous sheet or strip with longitudinal borders defining the flow path of the sample, where each of the sheets and strips is in fluid communication, e.g. overlapping, with adjacent strips. Alternatively, a plurality of strips may be employed, where the strips will be in different planes and overlapping, desirably at least partially staggered to minimize the thickness of the assembly and adhere each of the sheets and/or strips to the support. Thus, one could have a sample application or receiving strip, a cell removal strip, and one or more reagent strips in a staggered array, with each strip overlapping the next strip, so that the total thickness of the array is not more than about three strip thicknesses. The cell removal strip will usually extend substantially its full length over the reagent zone strip to ensure that all of the sample is received by the reagent zone. The transport material of the application zone may also have cell removal capability, so the cell separation zone may serve to remove residual cells from the sample. In this way, the cell separation zone may have relatively fine pores, since the substantially reduced number of cells will not clog the cell separation zone and substantially all of the red blood cells may be removed with minimal lysis.

The sample application zone will be a bibulous strip, which will receive the sample and pass the sample to the next strip. For the most part, the sample will involve blood. Since the red blood cells and the heme are colored, the presence of such components in the measurement region will obscure the boundary defining the amount of analyte. Therefore, where blood is the sample, there will be a strip comprising one or more membranes for filtering the blood and removing the red blood cells, without lysing the blood cells. Various filters have been reported for removing the red blood cells. See, for example, U.S. Pat. Nos. 4,987,085, 5,132,086 and 5,215,886, and copending application Ser. No. 08/006,597, filed Jan. 21, 1993.

Various techniques may be used to apply the sample, including touching a micropipet, capillary or the like to the application site. A blood sample may also be applied by directly transferring a few drops of blood from the user's finger to the application zone. Measurement of the sample is not required, as the amount of sample employed for the assay is restricted to the absorption volume of the assay zone (reagent and measurement zone).

A reagent zone, or several reagent zones, may be included in fluid communication with the sample application zone. The reagent zone(s) may take a number of forms, including sections of the bibulous assay strip downstream of the application zone. Alternatively, the reagent zone may be provided by a separate bibulous strip positioned with one end in fluid communication with the application zone and the other end in fluid communication with the measurement zone. Similarly, when several reagent zones are used they may take the form of separate bibulous strips positioned in the flow path with the ends of each strip in fluid communication with the ends of adjacent strips or having bibulous bridges connecting the zones. The sample is transferred from the application zone and, as appropriate the cell filtration zone, and through the reagent zones by wicking.

The measurement zone is a narrow strip downstream of the reagent zone, and may be an extended section of the assay strip downstream of the reagent zone or a separate bibulous strip in fluid communication with the reagent zone(s). The absorption volume of the narrow measurement zone is small so that a minimum amount of sample will be absorbed, for example about 1 to 25 μL, preferably about 2 to 10 μL.

The bibulous sheet comprising at least the measurement region is supported by a first supporting film, where parts or all of the sheet may be laminated to the supporting film without interference with the assay strip. A second supporting film is laminated to the exposed surface of the bibulous sheet. The lamination can be achieved using adhesive on one or both of the films, where a layer of adhesive may extend all or a part of the length of the bibulous sheet. The films may extend beyond the bibulous sheet in at least one direction for bonding to each other to provide an integral device, with the bibulous sheet protected. One of the supporting films has a sample port or aperture which exposes a portion of the application zone; alternatively, the application zone may extend beyond the edges of the supporting films to expose the application zone. The distal edge of the measurement zone has an air vent so that air may be released as the sample wicks through the assay strip. The air vent will usually be an aperture which is formed in the upper supporting film at the distal end of the measurement zone.

The entire flow path may have a length of about 5 to 150 mm, usually about 50 to 100 mm, conveniently about 65 mm in length. The sample application zone may be about 5 to 25 mm in length, more usually about 10 to 20 mm, conveniently about 15 mm long. The assay strip may have one or more reagent zones, each having a length between about 3 and 10 mm; conveniently, the reagent zones have a total length of 5 to 10 mm, particularly about 6 mm. The width of the sample zone, the blood separation membrane and the reagent zone is from about 5 to 30 mm, more usually about 10 mm, which may conveniently be the width of the device. The measurement zone comprises a major portion of the flow path and is usually about 50 mm in length, but may be between 25 and 100 mm in length, generally being at least about 50% of the total length of the assay strip, usually at least about 60%. The measurement region, the thin membrane strip between the parallel barriers, is generally between 0.25 to 1.5 mm in width, preferably between 0.75 to 1.25 mm wide, so that a minimal amount of sample is required for the assay. The thickness of the different zones may vary, with the thickness of the application zone being in the range of about 50 to 200μ, to provide an absorption capacity of about 10 to 100 μL, the thickness of the separation zone being in the range of about 100 to 250, the thickness of the reagent zone(s) being in the range of about 100 to 250μ, and the thickness of the measurement zone being in the range of about 100 to 250μ.

The device will be configured to be conveniently handled, packaged and used. The width of the device may be between 5 to 30 mm, conveniently 5 to 20 mm, particularly about 10 mm, while the thickness of the device may be in the range of about 0.25 to 2 mm.

Assembly of the assay strip is readily achieved by applying an adhesive to at least a portion of the first supporting film and laminating a bibulous sheet comprising at least the measurement zone of the assay strip to a portion of the supporting film, where the adhesive is chosen so as not to interfere with the function of the assay strip. Convenient adhesives include 3M 9460, 3M 415 and 3M 443. The application zone may then be adhered to the supporting film with the application zone in fluid communication with the reagent zone of the assay strip.

For the multilayered assay strip, a reagent zone strip is aligned with a lower edge of the measurement zone strip, partially overlapping one end of
the measurement zone region, and laminated to the supporting film by means of the adhesive on the film. The reagent zone usually includes only one reagent zone, but may include additional reagent zones as individual strips, each overlapping the previously applied reagent strip or as a single strip with discrete areas having different reagents of the detectable signal system. A separation membrane for removing red blood cells and the like may be applied to the supporting film, with the separation membrane preferably being substantially superimposed over the reagent membrane, leaving a small area, less than about 25% of its length exposed for lamination to the film support. A sample receiving zone transport material is laminated to the supporting film with the material overlapping, and preferably substantially extending over, the separation and reagent strips, with a substantial portion extending beyond the separation strips in the direction away from the measurement strip, usually at least about 30% of its length, and may be 50% or more. The non-overlapping portion is laminated to the film support by means of the adhesive. Instead of using adhesive, other laminating techniques may be used, such as ultrasonic welding, heat lamination or solvent bonding.

The sample receiving zone, separation strip and reagent strip may be applied as a bibulous sheet and are conveniently the same width as the entire assay device. The individual strips of the measurement region would then be delineated with liquid impervious barriers. The measurement region is thus defined by application of two liquid impervious barriers to define the assay strip or the strips may be previously treated with the liquid impervious barrier material and the strips indexed so as to the have the zones properly aligned to define the assay strip.

Either prior to applying the strips to the first support or prior to the application of the second supporting film, the assay strip is formed by providing a pair of liquid impermeable barriers beginning at least at the upper edge of the reagent strip and extending through the measurement membrane. Greater flexibility is allowed as to the capacity of the application strip and separation strip, since the amount of sample which is used in the assay will be defined by the volume passing through the reagent strip and received by the measurement strip. Thus, the absorption capacity of the application strip will usually be larger than the combined absorption capacity of the reagent and measurement strips, but need not be, since the liquid sample can provide a reservoir in the sample port. The liquid impervious barriers prevent flow of the sample from the assay strip to the unused portion of the bibulous or membrane sheets. The barriers are preferably formed by hydrophobic printing, but may be formed by laser cutting, etching or melting, die cutting, ultrasonic staking or welding, or the like, depending on the nature of the material forming the assay strip and reagents involved in the various zones.

The strips and bibulous sheets may be initially laminated to the upper or lower support. The upper support may have been modified prior to the lamination to introduce various ports, vents, printed matter or the like. Alternatively, some or all of this processing may be done after adhering the strips and bibulous sheets to the upper support.

The second supporting film is secured to the laminated assembly by an adhesive, ultrasonic bonding or staking, heat sealing, solvent bonding or the like. As necessary, a sample port is formed in the upper supporting film and is positioned to expose a portion of the application zone for application of the sample, preferably a non-overlapping portion of the application zone in relation to the separation and reagent membranes. A scale or other markings may be printed on the upper supporting film for use in reading and interpreting the results of the assay. The laminated assembly may include a plurality of individual assay strips, and may be separated into the individual assay strips by the impervious barrier. Alternatively, each assay strip may be individually formed.

The detectable reagent system may comprise a variety of reagents diffusively or non-diffusively bound on the bibulous strip, depending upon the analyte in question, the nature of the sample, the type of result desired (semi-quantitative or quantitative) and the chemistry employed. The members are for the most part bound on the reagent zone and/or the measurement zone, although in some instances, the application zone and separation zone may have one or more reagents. The measurement zone may have enzyme substrates, antibodies, binding partners, ligands, antigens and/or reactive chemicals diffusively or non-diffusively bound in a predetermined distribution, usually a uniform coating. The reaction between the members of the detectable signal system with an analyte in a sample produces a detectable signal which is visible in the measurement zone. For a quantitative result, the detectable signal takes the form of a detectable boundary, with the height of the boundary providing an indication of the amount of analyte within the sample.

The detectable signal reagent system may include a conversion reagent in the reagent zone which reacts with the analyte in the blood to produce a stoichiometric amount of an intermediate product. The intermediate product directly or indirectly reacts with another member of the detectable signal reagent system bound to the continuous flow path or strip downstream of the conversion reagent, producing a detectable signal on the path or strip. Additional reagents may be diffusively or non-diffusively bound along the flow path to produce a detectable signal, such as catalysts or other intermediate components.

A number of analytes, particularly cholesterol and glucose, are substrates with oxidases to produce hydrogen peroxide when testing for the amount of cholesterol or glucose in blood. As illustrative, for cholesterol, the conversion reagent usually includes reagents which react with the various forms of cholesterol in the blood, e.g. cholesterol and cholesterol esters, to form hydrogen peroxide. The preferred conversion reagents are cholesterol esterase (EC:3.1.1.13) and cholesterol oxidase (EC:1.1.3.6). The cholesterol ester is hydrolyzed by the cholesterol esterase, while the cholesterol oxidase accomplishes oxidation of the cholesterol to produce a stoichiometric amount of hydrogen peroxide. The hydrogen peroxide reacts in turn with a peroxidase substrate in the presence of horseradish peroxidase to form a reactive intermediate which reacts with a compound bound in the measurement zone to produce a colored region on the flow path which indicates the level of cholesterol in the sample.

The cholesterol esterase is preferably immobilized at about 15–20 units/ml, but may be immobilized at about 5 to 50 units/ml. The cholesterol oxidase may be immobilized at 20 to 100 units/ml, most preferably at 40–60 units/ml. The horseradish peroxidase may be immobilized along the flow path of the assay strip, normally being present at about 5 $\mu$g/ml, but may be at 1–100 $\mu$g/ml. The immobilized dye will be immobilized at about 4 mg/ml, but may vary from about 1–10 mg/ml, while the diffusible dye will be present at about 0.1–1 mg/ml. The diffusible dye will be present in at least one of the reagent zone and the measurement zone. The horseradish peroxidase will be in at least one of the reagent zone and the measurement zone. The cholesterol oxidase and esterase will be in the reagent zone and may be in the upstream portion of the measurement zone. The detectable signal reagent system may appropriately include members which produce visually observable color fronts for a quantitative assay. See, for example, U.S. Pat. Nos. 4,959,324 and 5,132,086.

The detectable signal reagent system may also include additional reagents to promote the accuracy and reliability of the assay. For example, an appropriate detergent may be present for disrupting lipoprotein and making the cholesterol and cholesterol ester rapidly available for reaction with the esterase and oxidase enzymes. Non-ionic, anionic, or cationic detergents, etc. may be employed. Detergents of particular interest include polyoxyalkylenes, ethoxylated alkylphenols, octyl-phenoxypolyethoxyethanol, octylphenol-ethylene oxide condensates and polyexyehthylene lauryl ethers, or anionic detergents such as bile acids. Gum arabic or other sticking agents or adhesives may be employed. Various reagents may be employed to inhibit interference between the sample and the detectable signal producing system. For example, when hydrogen peroxide is employed as a reagent, a chelating agent, particularly a hydroxylated carboxylate, a metal oxide oxidant, particularly stannate, nitroprusside, and a catalase inhibitor, particularly sodium azide, may be employed. See, U.S. Pat. No. 5,155,025. Substantially non-interfering proteins are also of interest, such as gelatin, casein, serum albumin or gamma-globulins. Preservatives, such as sucrose, polyvinyl alcohol, polyvinyl pyrrolidone, or dextran, may be present in the regions which include reagents. Any convenient buffer may be employed for impregnating the strip with the reagents, preferably a substantially dilute buffer which may include phosphate, TRIS, MOPSO, borate, carbonate and the like. The buffered solution will be at a pH in the range of 4.5 to 8.5, most usually 6.5 to 7.5, and have a concentration in the range of 0.01 to 0.2M, most usually 0.025 to 0.1M.

The control flow path is preferably substantially similar to the sample flow path. The control flow path generally includes a control zone, at least one reactant zone and a measurement zone where the control zone is analogous to the sample receiving zone. The general configuration and organization of the control strip is analogous to the sample assay strip. Components of a signal producing system are impregnated in one or more of the control, reactant and measurement zones. The signal producing system is preferably substantially similar to and in the same arrangement as in the sample flow path. Usually, one will have a predetermined amount of analyte or member of the signal producing system in the control flow path. For example, where hydrogen peroxide is produced as part of the assay, one could have a known amount of one or more reactive compounds (e.g. cholesterol, cholesterol ester or glucose, etc.) and the appropriate enzymes in the control and reagent zones upstream from the measurement zone. The control transports the reactive compound along the flow path. The analyte may be removed from the sample, with the analyte free sample matrix providing the control.

The reagent and measurement zones of the control flow path are preferably substantially similar to the reagent and measurement zones of the sample flow path. For example, the control path reagent zone and the control path measurement zone for a cholesterol assay will comprise the same members of the signal producing system as the sample path reagent and measurement zones. The members of the signal producing system of the control flow path react with the reactive compound to produce a detectable signal. The height of the detectable signal indicates the amount of reactive compound transported to the measurement zone. If the signal is within an acceptable range, the assay is verified.

Various approaches may be employed for the control assay, depending upon whether a fluid separate from the sample is used to provide for the control reaction. If a fluid separate from the sample is used, such as the addition of water or a buffered solution to the control path, then the application zone may be impregnated with cholesterol and/or cholesterol ester in the application zone. Alternatively, one may use any other source of hydrogen peroxide, such as a combination of glucose and glucose oxidase, where these reagents may be placed in the application and/or reagent zones. This can be achieved using a different bibulous strip for the control zones or applying the cholesterol source or other reagents to the control site after assembly of the assay strip.

If the sample is to be used as the fluid for the control assay, then one may use a cholesterol source in the application zone and the control will be the differential between the sample measurement zone and the control measurement zone.

In one embodiment of the control, the analyte is removed from the sample to provide an analyte free sample matrix which is used for the control. The analyte may be removed by removing or otherwise deactivating the naturally occurring analyte so that it will not react with the control path signal producing system to produce a detectable signal. Various means may be employed to remove or deactivate the analyte, including an antibody to the analyte, an analyte deactivating enzyme, or both. When the analyte is cholesterol, an antibody to cholesterol or a cholesterol deactivating enzyme such as a kinase or other esterifying enzyme may be used. The removal or deactivation agents would be impregnated in the control application zone. The sample may be transported from an application site to both the control flow path and the sample flow path. Alternatively, if the assay strip includes two sample ports, sample may be separately applied to each sample port. The upper supporting film may include a control path sample port in addition to the sample port for the sample flow path. Alternatively, for some applications one sample port may be employed for both the sample and control flow paths.

Various compounds may be used to produce hydrogen peroxide and approximate the assay protocol: with cholesterol, cholesterol oxidase; with cholesterol ester, cholesterol esterase and cholesterol oxidase; with glucose, glucose oxidase; with urea, urea oxidase, etc. A peroxidase and appropriate dye intermediate are also employed. The height of the visual signal indicates the amount of the reactive compound present. If the detectable signal is within an acceptable range, the assay determination is verified.

The assay strip may consist of one or more of any of a number of bibulous materials. Examples of materials which may be employed include paper, synthetic membranes such as nitrocellulose, cellulose acetate or regenerated cellulose, hydrophilic treated polyethylene or polypropylene, or synthetic screen materials. Appropriate synthetic screens include those with fibers of polyester, nylon, polypropylene, synthetic plastics, or a combination of plastics. Screens may also be made of natural fibers, for example cotton. The fibers may be monofilament or multifilament, and the screen may have a square weave, a twill weave, or a plain reverse Dutch weave, or any combination of weave type. The mesh opening may be about 5 to 250 microns, but is usually about 10 to 100 microns. The sample application zone is composed of any conventional bibulous material that can move whole blood rapidly without significant lysis.

The cell separation strip will be an appropriate membrane for removing red blood cells with minimal lysis. A number of membrane systems have been described in the literature. Glass fibers and combinations of membranes have been reported to be useful in U.S. Pat. Nos. 4,477,575; 4,816,224; and 4,987,085. These membranes may be included in the assay strip as small strips, which may be of the desired dimensions for the assay strip or wider or may be parts of extended rolls, which may be used during manufacture with the other sheets and restricted in size by liquid impervious barriers.

The support material may be any convenient nonabsorbent material. The nonabsorbent material may provided in the form of a sheet or roll having a thickness of from about 0.05 to 1.5 mm, usually in the range of about 0.1 to 1 mm. Suitable nonabsorbent materials include a plastic material such as polycarbonate, acetate, low or high density polyethylene, polyester, vinyl and the like. Other nonabsorbent materials which may be employed include nonabsorbent paper and cardboard, metal and plastic. A nonabsorbent material such as cellulose acetate having a thickness of 0.25 mm is conveniently used for the supporting film.

Immunoassays can be performed where the analyte is a ligand, e.g. a hapten or antigen, or a receptor, where the ligand and receptor form a specific binding pair ("SBP"). In a simple protocol, labeled analyte would be in the reagent zone, where analyte and labeled analyte would compete for the complementary SBP in the measurement zone. By "labeled analyte" is intended any moiety which can compete with the analyte for binding the complementary SBP in the measurement zone. Usually, the label will be an enzyme. By coating the surface of the support(s) above and/or below the bibulous strip comprising the measurement zone with a soluble substrate, the substrate will be dissolved by the assay medium and react to form a colored product. Alternatively, or in combination, the substrate may be diffusibly impregnated in the bibulous strip with the complementary SBP. The amount of SBP will vary with the concentration range of interest of the analyte, the length of the measurement zone, the density of the SBP required to provide a discernible color front, and the like. See U.S. Pat. No. 4,959,324.

The subject invention is now considered in light of the drawings which depict preferred embodiments of the present invention. In a preferred embodiment shown in FIGS. 1 to 3, a laminated assay device for performing a quantitative assay is provided. The assay device has first (upper) and second (lower) supports or supporting films 8 and 10 laminated to a bibulous assay strip 12 by a pair of adhesive layers 14. The support members 8 and 10 extend across the front and back surfaces of the assay strip 12. The first support 8 has an air hole 16 formed at the distal end of the assay strip 12 for releasing air from the device, thereby allowing wicking of the sample through the assay strip 12. Once the wicked sample has reached the air hole 16, further absorption of the sample is prevented.

Figure 1:
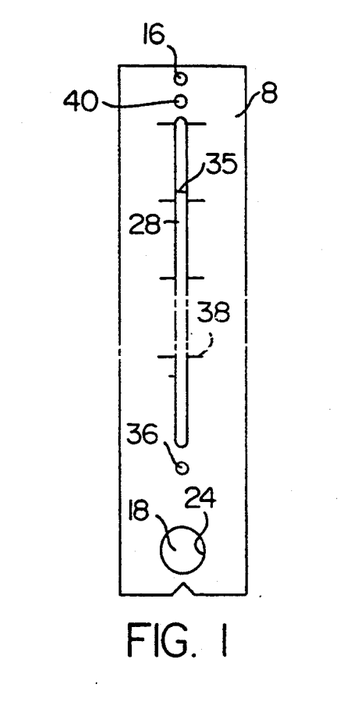
FIG. 1 is a front plan view of an assay device according to this invention.
Figure 2:
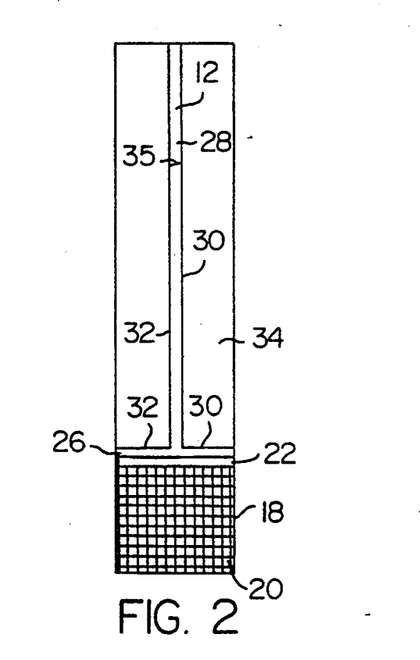
FIG. 2 is a front plan view of the assay device of FIG. 1 with the front support removed.
Figure 3:
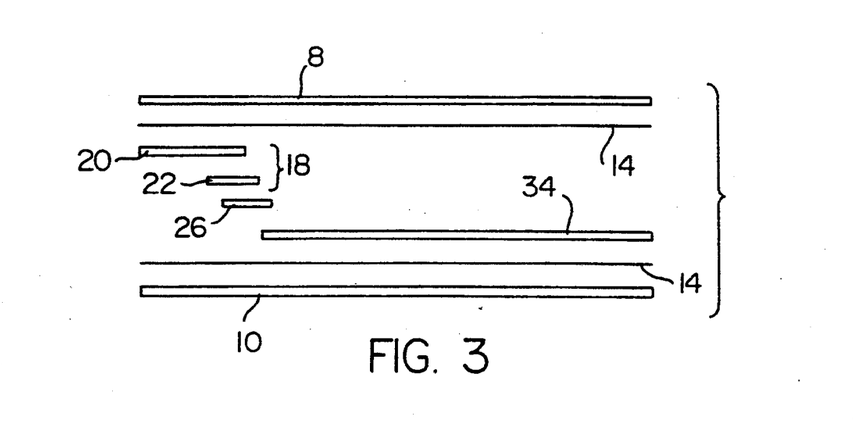
FIG. 3 is an exploded elevational side view of the assay device of FIG. 1.

In the preferred embodiment, the assay strip 12 includes a sample application zone 18 provided by a transport material 20 and a cell separation membrane 22. A portion of the application zone 18 is exposed to sample addition through a sample port or aperture 24 in the first support 8. The sample is deposited on the exposed portion of the transport material 20 and transported to the separation membrane 22 via wicking. The separation membrane 22 filters the sample as it travels through the application zone 18 to remove substantially all of the red blood cells.

A reagent strip 26 is positioned downstream from the application zone 18, overlapping a major portion of the separation membrane 22. The reagent strip 26 is impregnated with one or more members of the detectable signal reagent system. For example, for a cholesterol assay one has cholesterol esterase and cholesterol oxidase for reacting with the cholesterol and any esters to produce hydrogen peroxide. There may be one or more reagent zones which are overlapping or in tandem on the same or different strips, where the same or different reactions may occur in each of the zones. Building on the same example, one could have cholesterol esterase in a first zone, cholesterol oxidase in a second zone, and horseradish peroxidase in a third zone.

The sample is transported from the application zone 18 through the reagent strip 26 by wicking, reacting with any reagents bound in the reagent strip 26. This reaction may produce intermediate members of the detectable signal reagent system, such as when performing an assay to determine the presence of an analyte such as cholesterol or glucose.

Downstream from the reagent strip 26 is a measurement zone 28 defined by a pair of liquid impervious barriers 30 and 32 formed by hydrophobic printing. The liquid impervious barriers 30 and 32 separate the measurement zone 28 from unused portions of a bibulous sheet 34. The measurement zone 28 is substantially narrow in width, on the order of 0.25 to 1.5 mm, minimizing the amount of sample required for the assay. The sample is transported to the measurement zone 28 from the reagent strip 26 by wicking. The measurement zone 28 includes one or more of the members of the signal producing system, and includes a dye forming precursor throughout the region to produce a colored front which is related to the amount of the analyte in the sample. For example, when determining the amount of cholesterol in a sample, the measurement zone 28 may be impregnated with horseradish peroxidase which reacts with hydrogen peroxide in the presence of an electron donor component and dye coupling agent. An electron donor coupling agent which reacts with hydrogen peroxide in the presence of peroxidase may also be present in the measurement zone 28. As the sample wicks through the measurement zone 28, a border 35 forms indicating the exhaustion of the hydrogen peroxide. The height of the border 35 is related to the level of cholesterol in the sample.

The first support 8 may be opaque at other than viewing sites and is imprinted with a test indication window 36, a calibrated measurement scale 38 and a test complete window 40. The test indication window 36 displays a color change indicating that the assay is in progress. The calibrated measurement scale 38 extends along the measurement zone 28 for ease of determination of the height of the colored border 35 and the amount of analyte in the sample, such as the cholesterol level. The test completion window 40 positioned at the distal end of the assay strip 12 displays a color change indicating when the assay is completed.

In order to carry out an assay to determine the presence or amount of an analyte, for example cholesterol, the user lances a finger and applies a hanging drop of blood to the sample port 24. Sample is transported from the transport material 20 through the separation membrane 22, reagent zone 26 and the measurement zone 28 by wicking, filling the measurement zone 28 with processed sample and forcing air through the air hole 16 until sample reaches the air hole 16. The cholesterol in the sample reacts with the cholesterol esterase and cholesterol oxidase enzymes bound in the reagent zone 26 producing hydrogen peroxide. The hydrogen peroxide produced by the enzyme and cholesterol reactions in turn reacts with horseradish peroxidase present in the assay strip 12 to produce a dye precursor which in turn reacts with a coupling compound to produce a detectable signal in the measurement zone 28.

When the test completion window 40 changes color, the assay is completed and the result may be read. There may be a short wait period of not more than about 15 min to allow the color to fully develop. The reaction of the reagents with the sample results in a colored region with a clearly defined boundary 35 in the measurement zone 28. The colored boundary 35 is related to the amount of cholesterol within the sample, providing an indication of the user's cholesterol level. The entire assay including reading the results and verifying the assay may be completed in less than 30 minutes, frequently in less than about five min.

Figure 4A:
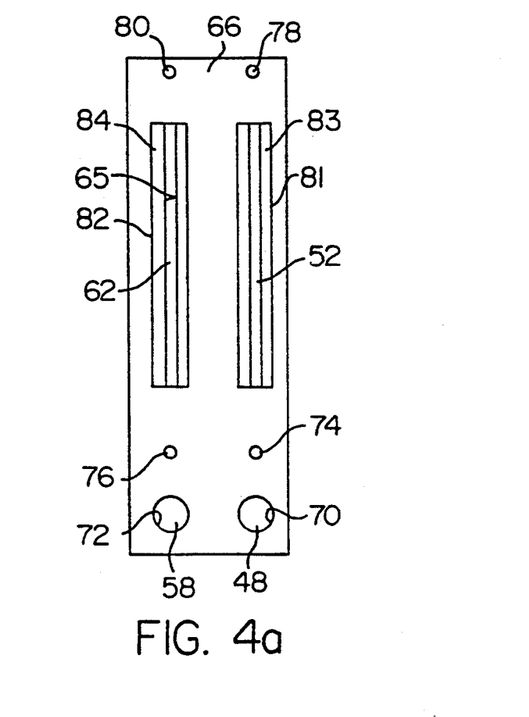
FIG. 4a is a front plan view of another embodiment of an assay device.
Figure 4B:
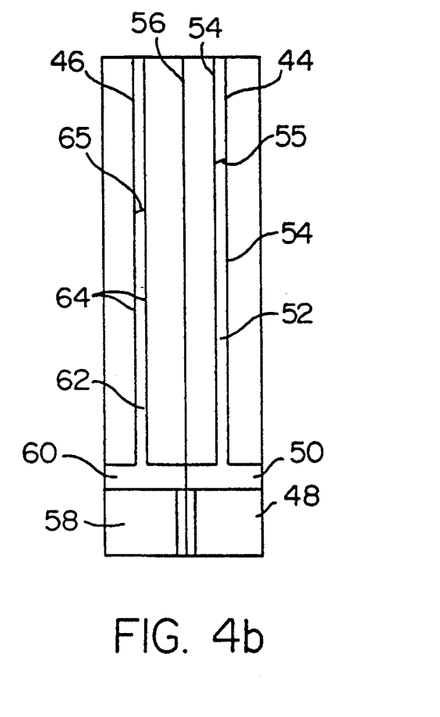
FIG. 4b is a front plan view of the assay device of FIG. 4a with the front support removed.
Figure 4C:
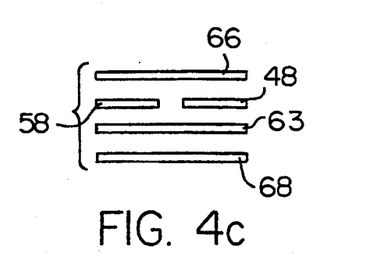

Another preferred embodiment of an assay device for performing a quantitative assay is provided in FIGS. 4a to 4c. The assay device includes a bibulous assay strip 44 and a bibulous control strip 46. The assay strip 44 includes a sample application zone 48 (includes a cell separation zone, not shown) and a single strip having a reagent zone 50 and a measurement zone 52 defined by a pair of liquid impermeable barriers 54. The members of a detectable signal producing system are diffusively or non-diffusively bound in the reagent zone 50 and the measurement zone 52 as with the previous embodiment. Sample is transported through the application zone 48 and the reagent and measurement zones 50 and 52 by wicking, with the sample reacting with the members of the detectable signal reagent system to produce a colored boundary 55.

The control strip 46 is separated from the assay strip 12 by a liquid impermeable barrier 56, and includes a sample application zone 58 and a single strip having a reagent zone 60 and a measurement zone 62 defined by liquid impermeable barriers 64. The sample application zone 58 may be impregnated with an antibody to the analyte or an analyte deactivating enzyme and a reactive compound downstream of the antibody or analyte deactivating enzyme. The reagent and measurement zones 60 and 62 are preferably impregnated with the same members of the detectable signal system as the assay strip 44. As is shown particularly in FIG. 4b, the assay strip 44 and the control strip 46 are provided by isolating sections of a bibulous strip 63 having a reagent zone and a measurement zone. Alternatively, the assay strip 44 and the control strip 46 may be provided by a bibulous assay strip and a bibulous control strip, respectively. The assay and control strips 44 and 46 may alternatively be provided on a single sheet by isolated strips. As sample is transported through the application zone strip 58 of the control strip 46, the naturally occurring analyte is removed. The reactive compound impregnated in the application zone 58 downstream of the inactivating agent will be transported through the reagent and measurement zones 60 and 62 by the analyte free sample, where the reactive compound reacts with the members of the detectable signal system to produce a detectable signal or colored boundary 65.

First and second supporting films 66 and 68 are laminated to the front and back surfaces of the assay and control strips 44 and 46 by adhesive (not shown). The supporting films 66 and 68 are formed of a transparent, substantially nonabsorbent material. The first supporting film 66 includes an assay supply port 70 and a control supply port 72 exposing portions of the application zone 48 and 58 of the assay strip 44 and control strip 46, respectively. Air holes 78 and 80 are provided at the distal end of the measurement zones 52 and 62. Sample is applied to both sample ports 70 and 72, and is transported through the assay strip 44 and control strip 46 by wicking until the sample reaches the air holes 78 and 80, thereby filling the measurement zones 52 and 62 with a measured amount of sample.

Test indication windows 74 and 76 display a color change to indicate that the sample and control assays are in progress, while the air holes 78 and 80 serve also as test completion windows and display a change in color signalling the completion of the assay. Test windows 81 and 82 allow for observation of the test result. The test windows 81 and 82 have lenses 83 and 84 formed in the support film 66 to sharpen the appearance of the boundary. A scale as previously described may be provided to measure the distance of the boundary.

Figure 5:
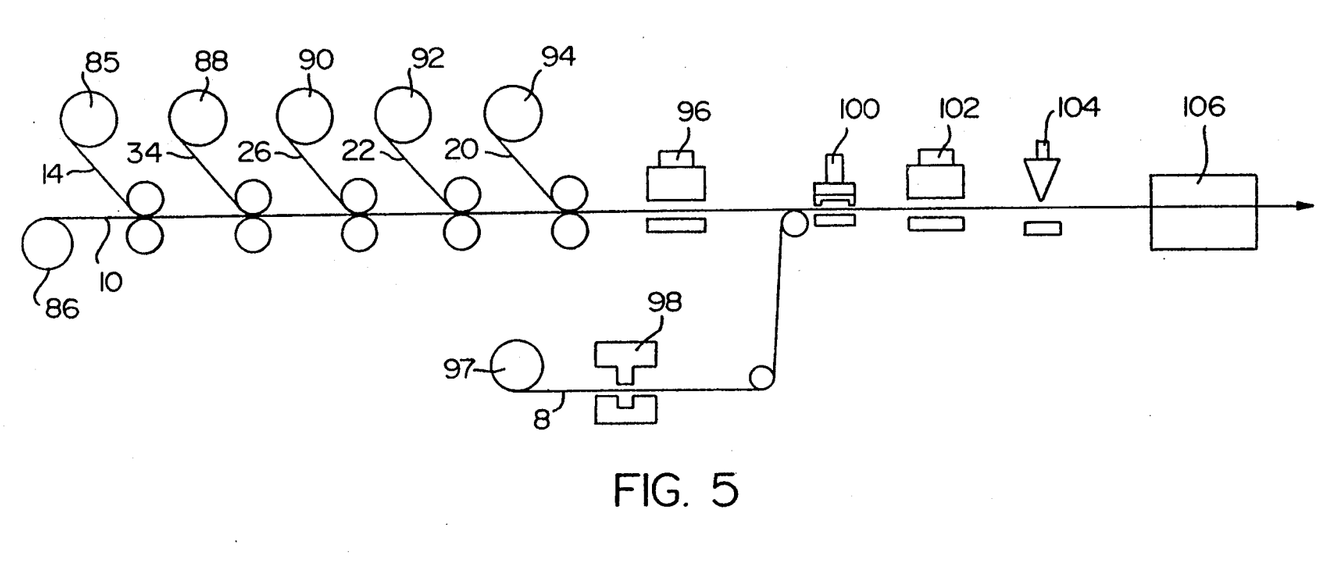
FIG. 5 is a schematic diagram of the procedure for assembly of an assay device.
Figure 6:
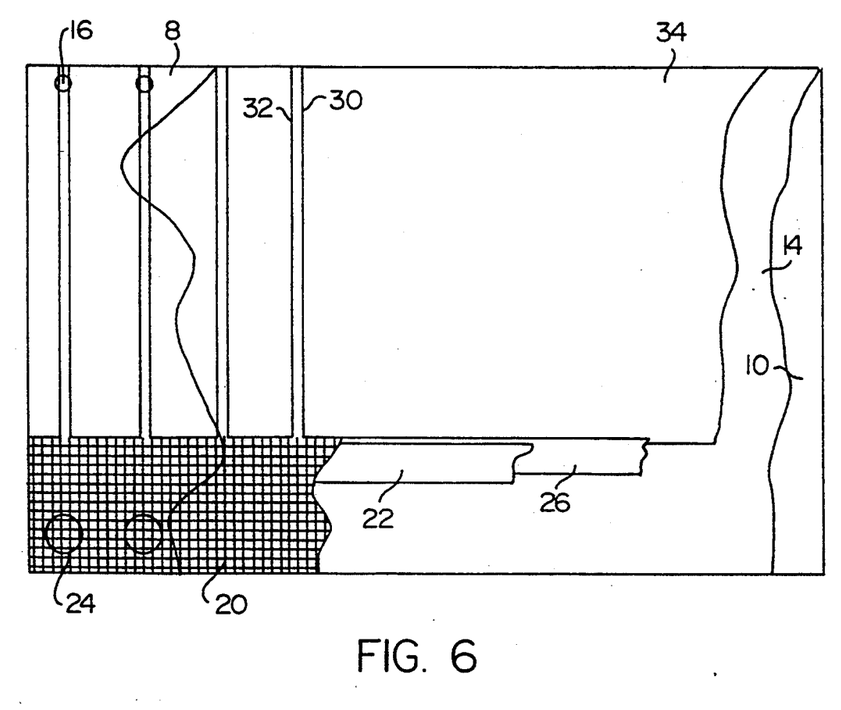
FIG. 6 is a diagrammatic view of the assembly of strips, shown with several elements of the assay device broken away.

The various stages of preparing an assay device are diagrammatically indicated in FIGS. 5 and 6. In the first stage, an adhesive layer 14 from adhesive supply 85 is laminated to a sheet of supporting film 10 drawn from a film supply 86. A sheet of measurement strip 34 is removed from the a measurement strip supply 88 and laminated to a major portion of the supporting film 10, as is depicted in FIG. 6. A sheet of the reagent strip 26 from a reagent strip supply 90 is applied overlapping a lower edge of the measurement strip 34. A sheet of the separation strip 22, provided on a separation membrane supply 92, is positioned substantially across the reagent strip 26 and laminated to the supporting film 10. The transport material 20 drawn from a transport material supply 94 is laminated to the supporting film 10 substantially covering the separation membrane and reagent strip 22 and 26, respectively. The transport material 20 and separation membrane 22, and reagent and measurement strips 26 and 34 are positioned in fluid communication with the adjacent strips to provide a continuous flow path.

The laminated assembly passes through a barrier forming station 96 for formation of the liquid impervious barriers 30 and 32 to define the measurement zone 28 and as appropriate the other zones. A sheet of the supporting film 8 from support supply 97 passes through a punch station 98 for the formation of supply port 24 and air hole 16 and is applied to the laminated assembly. The supporting film is secured in place at lamination station 100 by heat staking. The test indication window 36, measurement scale 38, test completion window 40 and any additional information is imprinted on supporting film 8 at printing station 102. The laminated assembly is separated into individual assay devices by cutting station 104, and the individual assay devices are inserted into sealed containers at finishing station 106.

The upper film may be prepared with the necessary vents and printing prior to assembly, and the assembly line run so as to properly position the vents and windows in relation to the assay strip. By appropriate orientation of the rolls and control of the movement of the various sheets from the rolls, one can have the upper strip properly positioned automatically, so that upon final assembly, the various elements of the device are properly spatially related. Also, while FIG. 5, shows the various rolls in tandem relationship on the assembly line, alternatively, the rolls could be positioned in the same plane orthogonal to the movement of the sheets, positioned to lay down the individual sheets on the supporting film in the correct positions.

For the assay device having a control strip, the measurement zones may be the same for the sample and control assay strips. Differences would be associated with the application zone and the reagent zone. As indicated previously, one may wish to have an analyte inactivator at the control application zone and a source of analyte equivalent in the application zone or reagent zone. These modifications in the sheets used for the various zones may be achieved by adding the necessary reagents at the sites on the sheets where the control assay strip will be defined by the liquid impervious barriers. Alternatively, one need not have a continuous sheet, but may have individual strips alternating for the sample and control assay strips.

It is apparent from the foregoing that the laminated assay device provides an efficient and accurate method of performing a non-instrumented assay for detecting the presence or amount of an analyte. The assay device is self-contained. The size of the sample is minimized, increasing the speed and accuracy of the assay and the convenience of the user. The measurement zone determines the amount of sample required for the assay, which need not be measured by the user. The control strip provides a simultaneous control verifying the accuracy of the assay. In addition, the device may be manufactured in a manner which allows for high reproducibility in a run, where the materials are uniform and are uniformly manipulated, so that large batches of devices can be produced substantially automatically.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teaching of this invention that certain changes and modifications may be made thereto without departing from the spirit or scope of the appended claims.

What is claimed is:

1. An assay device for performing an assay to determine an analyte in a sample, said device comprising:

upper and lower inert supporting films fastened at their edges, said upper film having a sample port and an air vent; positioned between said supporting films at least one bibulous sheet having a width extending substantially the full width of said films;

said bibulous sheet comprising an assay strip comprising an application zone for receiving said sample and a separation zone for seperating cells from blood, a reagent zone comprising reagents of a signal producing system for producing a colored product; and a measurement zone comprising reagents of said signal producing system for producing a boundary whose distance along said assay strip is related to the amount of analyte in said sample, wherein at least said measurement zone extends at least a major portion of the length of said bibulous sheet and is defined by liquid impervious barriers and is of substantially narrower width than said bibulous sheet;

wherein the absorption capacity of said assay strip determines the amount of sample which is analysed.

2. A device according to claim 1, wherein said at least one bibulous sheet comprises a single sheet comprising said reagent zone and said measurement zone and a second sheet comprising said application zone and said cell separation zone.

3. A device according to claim 1, wherein said at least one bibulous sheet comprises partially overlapping bibulous sheets, including a sample application sheet overlapping a separation sheet overlapping a reagent sheet overlapping a measurement sheet.

4. A device according to claim 1, wherein said bibulous sheet is adhered to at least one of said support films by an adhesive.

5. A device according to claim 1, wherein said liquid impervious barriers are formed by hydrophobic printing or cutting.

6. A device according to claim 1, wherein said measurement zone has a volume absorptive capacity of from about 2 to 10 μl.

7. A device according to claim 1, wherein said width of said measurement zone is in the range of about 0.25 to 1.5 mm.

8. An assay device for performing an assay to determine an analyte in a sample, said device comprising:

upper and lower inert supporting films fastened at their edges, said upper film having a sample port and an air vent;

positioned between said supporting films at least one bibulous sheet having a width extending substantially the full width of said films and comprising a first sample assay strip and second control assay strip;

said assay strips comprising a sample application zone for receiving sample, a separation zone for separating cells from blood, a reagent zone comprising reagents of a signal producing system for producing a colored product, and a measurement zone extending at least a major portion of the length of said bibulous sheet defined by liquid impervious barriers and of a substantially narrower width than said bibulous sheet and comprising reagents of said signal producing system for producing a boundary whose distance along said assay strip is related to the amount of analyte in said sample, wherein the absorption capacity of said assay strips determines the amount of sample which is analysed and said control assay strip comprises an analyte inactivating agent and a known amount of an analyte or a substitute reagent system for producing said colored product.

9. A device according to claim 8, wherein said measurement zone has a volume absorptive capacity of from about 2 to 10 μl.

10. A device according to claim 8, wherein said width of said measurement zone is in the range of about 0.25 to 1.5 mm.

11. An assay device for performing an assay to determine cholesterol in a blood sample, said device comprising:

upper and lower inert supporting films fastened at their edges, said upper film having a sample port and an air vent;

positioned between said supporting films at least one bibulous sheet having a width extending substantially the full width of said films and comprising an assay strip;

said assay strip comprising a sample application zone for receiving said sample, a separation zone for separating cells from said blood, a reagent zone comprising cholesterol oxidase and cholesterol esterase, members of a signal producing system for producing a colored product, and a measurement zone extending at least a major portion of the length of said bibulous sheet defined by liquid impervious barriers and of a substantially narrower width than said bibulous sheet and comprising reagents of said signal producing system for producing a boundary whose distance along said assay strip is related to the amount of analyte in said sample, said signal producing system comprising horseradish peroxidase, an oxidizable dye coupling component and a dye coupling component non-diffusibly distributed in said measurement zone;

wherein the absorption capacity of said assay strip determines the amount of sample which is analysed.

12. A method for forming an assay device comprising the steps of:

laminating a bibulous material to a substantially non-absorbent first support, said bibulous material comprising a sample flow pathway having a sample application zone and a reagent zone;

forming first and second liquid impervious barriers extending from said reagent zone to a distal end of said bibulous material to define a measurement zone between said liquid impervious barriers and in fluid communication with said reagent zone; and laminating a substantially absorbent second support to said bibulous material, said first support, said bibulous material and said second support comprising a laminated assembly.

13. The method of claim 12, wherein said step of laminating a bibulous material comprises laminating a measurement membrane to said first support and laminating a reagent membrane to said first support partially overlapping said measurement membrane, said reagent membrane comprising said reagent zone.

14. The method of claim 13, wherein said step of laminating a bibulous material further comprises laminating a transport material to said first support partially overlapping said reagent membrane, said transport material comprising said sample application zone.

15. The method of claim 14, further comprising the step of laminating a separation membrane to said first support in fluid communication with said transport material and overlapping said reagent membrane.

16. The method of claim 12, wherein said step of forming liquid impervious barriers comprises one of hydrophobic printing or cutting.

17. The method of claim 12, and further comprising the step of separating said laminated assembly into a plurality of said assay devices.

18. The method of claim 12, wherein said liquid impervious barriers separate said measurement zone from the remainder of said bibulous material and wherein said step of forming liquid impervious barriers includes forming liquid impervious barriers between said zones and the remainder of said bibulous material.

19. The method of claim 12, wherein said step of laminating a substantially non-absorbent second support employs one of adhesive, ultrasonic welding, heat sealing, heat staking, chemical bonding and solvent bonding.

20. The method of claim 12, further comprising the steps of laminating a control membrane to a portion of said first support, said control membrane and said bibulous material comprising a control flow pathway adjacent to said sample flow pathway, and forming a liquid impervious barrier between said sample flow pathway and said control flow pathway.

* * * * *